US008092523B2

(12) United States Patent
Li et al.

(10) Patent No.: US 8,092,523 B2
(45) Date of Patent: Jan. 10, 2012

(54) PROSTHETIC HEART VALVES WITH FLEXIBLE LEAFLETS

(75) Inventors: XueMei Li, Shoreview, MN (US); Yi-Ren Woo, Woodbury, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 999 days.

(21) Appl. No.: 11/717,305

(22) Filed: Mar. 12, 2007

(65) Prior Publication Data
US 2008/0228264 A1   Sep. 18, 2008

(51) Int. Cl.
*A61F 2/24* (2006.01)
(52) U.S. Cl. ................ 623/2.17; 623/1.26; 623/2.19
(58) Field of Classification Search ......... 623/2.12–2.19, 623/2.38, 2.4, 1.26
See application file for complete search history.

(56) References Cited

U.S. PATENT DOCUMENTS

| | | | | |
|---|---|---|---|---|
| 3,574,865 A | * | 4/1971 | Hamaker | 623/2.34 |
| 4,470,157 A | * | 9/1984 | Love | 623/2.15 |
| 4,506,394 A | * | 3/1985 | Bedard | 623/2.38 |
| 4,687,483 A | * | 8/1987 | Fisher et al. | 623/2.14 |
| 5,147,391 A | * | 9/1992 | Lane | 623/2.18 |
| 5,163,955 A | * | 11/1992 | Love et al. | 623/2.15 |
| 5,910,170 A | | 6/1999 | Reimink et al. | |
| 6,454,799 B1 | * | 9/2002 | Schreck | 623/2.18 |
| 6,461,382 B1 | * | 10/2002 | Cao | 623/2.19 |
| 6,558,418 B2 | | 5/2003 | Carpentier et al. | |
| 7,445,631 B2 | * | 11/2008 | Salahieh et al. | 623/2.18 |
| 7,597,711 B2 | * | 10/2009 | Drews et al. | 623/2.11 |
| 7,803,186 B1 | * | 9/2010 | Li et al. | 623/2.19 |
| 2004/0122514 A1 | * | 6/2004 | Fogarty et al. | 623/2.14 |
| 2006/0095125 A1 | * | 5/2006 | Chinn et al. | 623/2.4 |
| 2006/0135964 A1 | * | 6/2006 | Vesely | 606/108 |
| 2006/0136052 A1 | * | 6/2006 | Vesely | 623/2.18 |
| 2006/0195185 A1 | * | 8/2006 | Lane et al. | 623/2.38 |
| 2007/0016288 A1 | * | 1/2007 | Gurskis et al. | 623/2.11 |
| 2007/0260305 A1 | * | 11/2007 | Drews et al. | 623/2.11 |
| 2008/0004696 A1 | * | 1/2008 | Vesely | 623/2.1 |

FOREIGN PATENT DOCUMENTS

WO    WO 2008/112243 A1 *  9/2008

* cited by examiner

*Primary Examiner* — Paul Prebilic
(74) *Attorney, Agent, or Firm* — Lerner, David, Littenberg, Krumholz & Mentlik, LLP

(57) ABSTRACT

A prosthetic heart valve of the type that includes a hollow annular stent and a plurality of flexible leaflets that are attached to the stent. One or more fixture structures are used to attach the leaflets to the stent so that sutures do not have to be used for that purpose. The fixture structures preferably extend annularly at least substantially all the way around the valve. Surfaces of the fixture structures that can come into contact with portions of the leaflets that move during use of the valve can be shaped to help beneficially shape those leaflet portions during their movements.

13 Claims, 4 Drawing Sheets

US 8,092,523 B2

PROSTHETIC HEART VALVES WITH FLEXIBLE LEAFLETS

BACKGROUND OF THE INVENTION

This invention relates to prosthetic heart valves, and more particularly to prosthetic heart valves having flexible leaflets and a stent structure for supporting and helping to shape the leaflets.

One well-known type of prosthetic heart valve includes a hollow, annular, stent structure to which a plurality (e.g., three) flexible leaflets are attached so that free edge portions of the leaflets can alternately move in toward and into contact with one another in the interior of the stent (valve closed condition), or out away from one another (valve open condition). In this type of valve the leaflets are typically attached to the stent by suturing. The suturing process is labor-intensive and the quality of the result is dependent on the skill-level of the individual operator. Suturing perforates the leaflet material and can potentially cause stress concentration, especially when placed at a location that experiences large operational stress. The tension applied by the suture is not controlled, which can affect the local geometry of the leaflet at the location of suture attachment. All of these factors can adversely affect the service life of the device.

SUMMARY OF THE INVENTION

In accordance with the invention, one or more fixture structures (which can be somewhat like a clip or clips) are used in lieu of sutures to secure the flexible leaflets of a prosthetic heart valve to the stent structure of the valve. For example, a portion of one of the leaflets of the valve may be placed over the blood-outflow edge of the stent between two annularly adjacent commissure regions of the stent. A fixture structure, which extends annularly at least substantially between those two commissure regions and which is shaped to mate with the stent blood-outflow edge between those commissure regions, is applied over the above-mentioned portion of the leaflet to secure the leaflet to the stent. The stent outflow edge portion and the fixture structure may be shaped to interengage (possibly through intervening leaflet material) so that the fixture structure is thereby held on the stent. Surfaces of the fixture structure that can be contacted by portions of the leaflet that move during use of the valve can be shaped to beneficially affect that leaflet motion. Any or all of the above structures and expedients can be used for all of the leaflets of the valve.

Further features of the invention, its nature and various advantages, will be more apparent from the accompanying drawings and the following detailed description.

DETAILED DESCRIPTION

Figure 1:
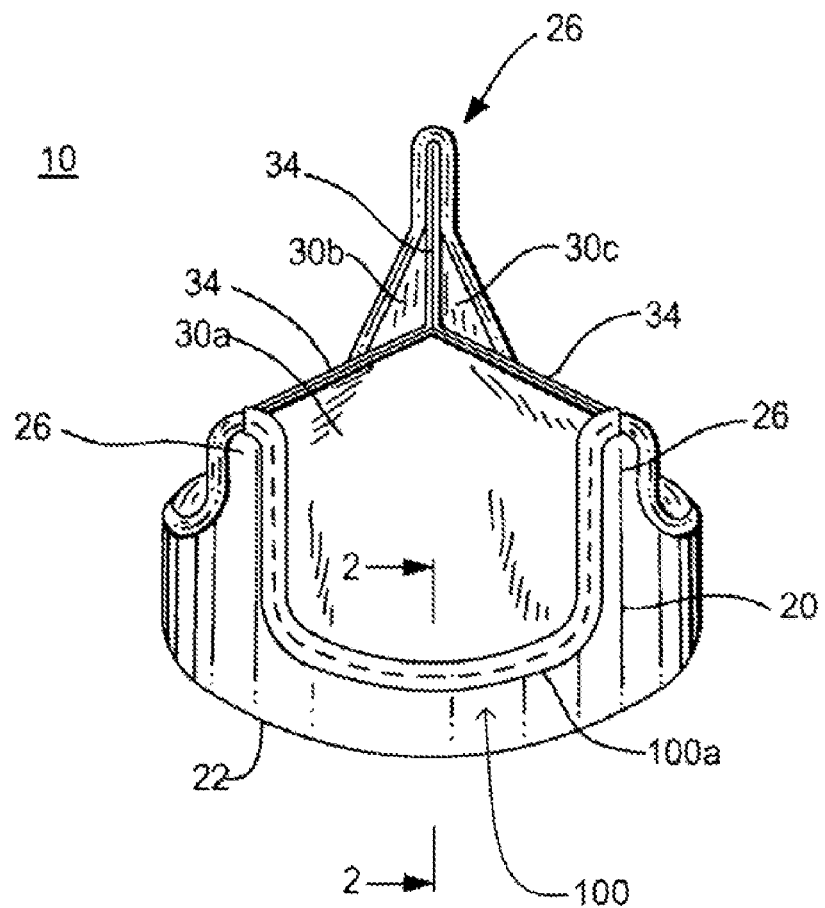
FIG. 1 is a simplified perspective or isometric view of an illustrative embodiment of a prosthetic heart valve that has been partly assembled in accordance with the invention.
Figure 2:
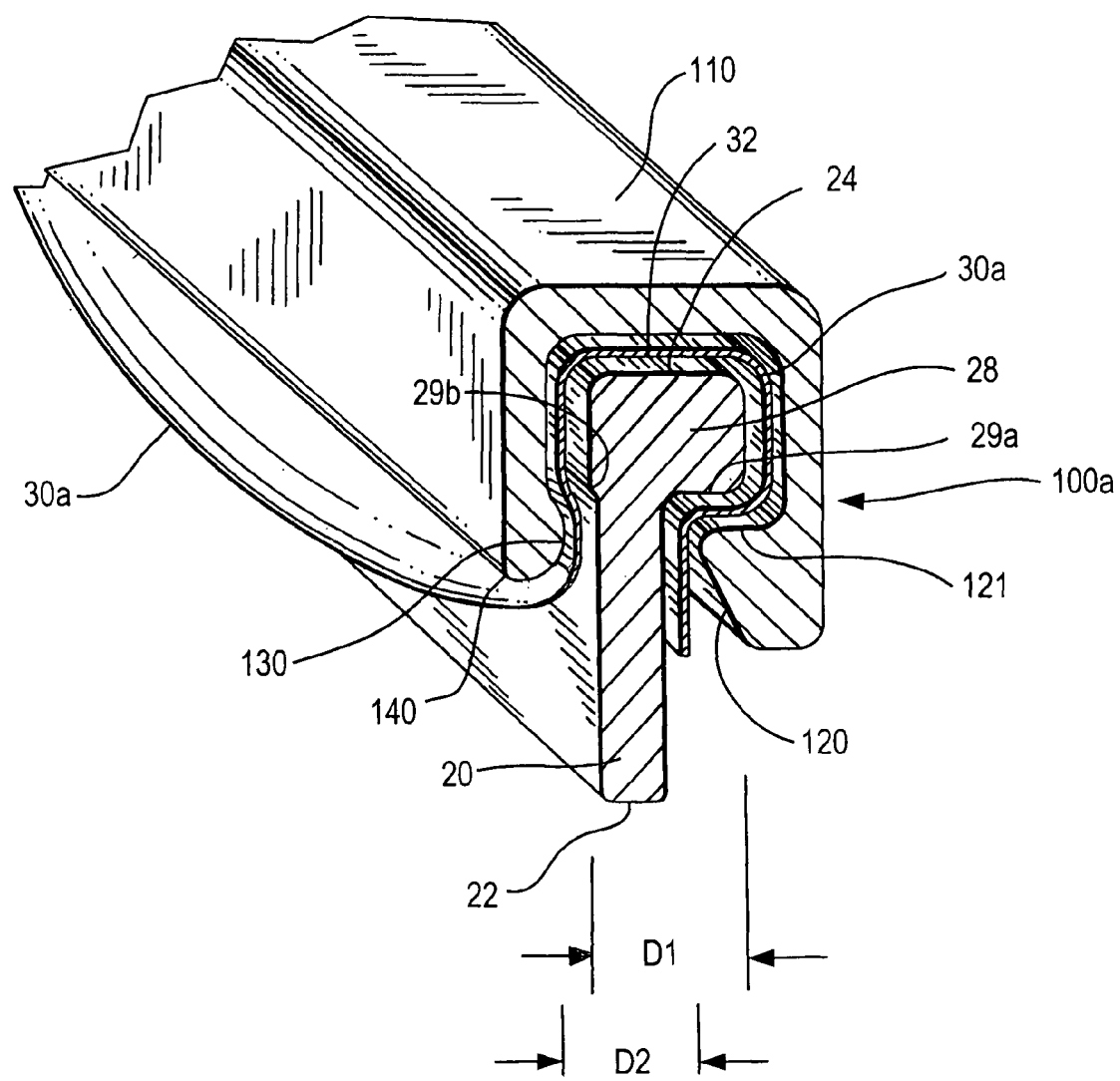
FIG. 2 is a simplified sectional view taken along the line 2-2 in FIG. 1.
Figure 3:
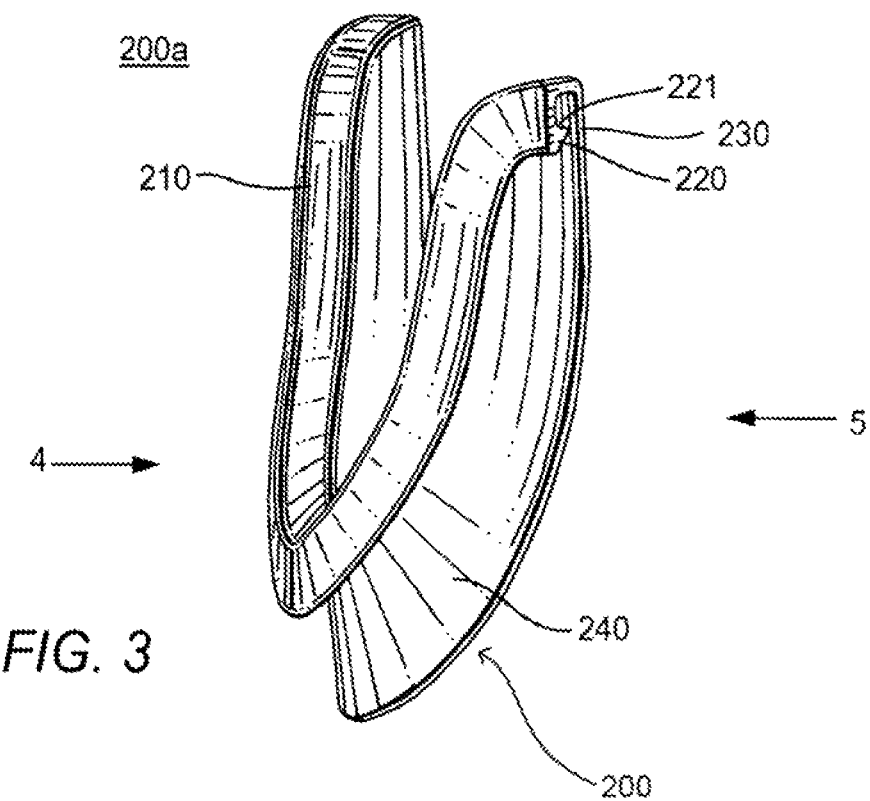
FIG. 3 is a simplified perspective or isometric view of a representative portion of another illustrative embodiment of the invention.
Figure 4:
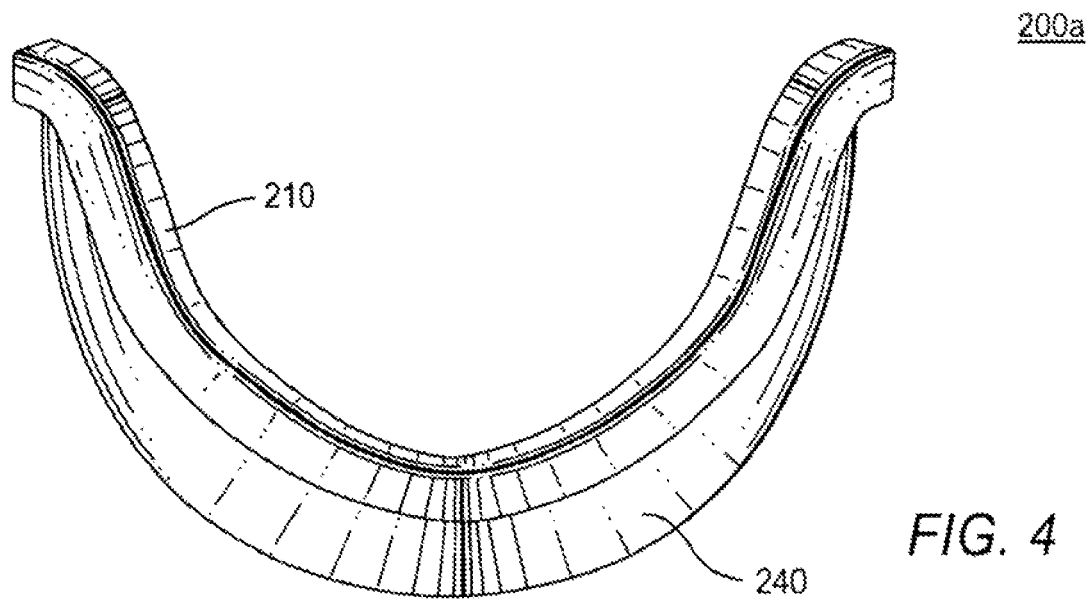
FIG. 4 is another simplified perspective or isometric view taken generally along the line 4 in FIG. 3.
Figure 5:
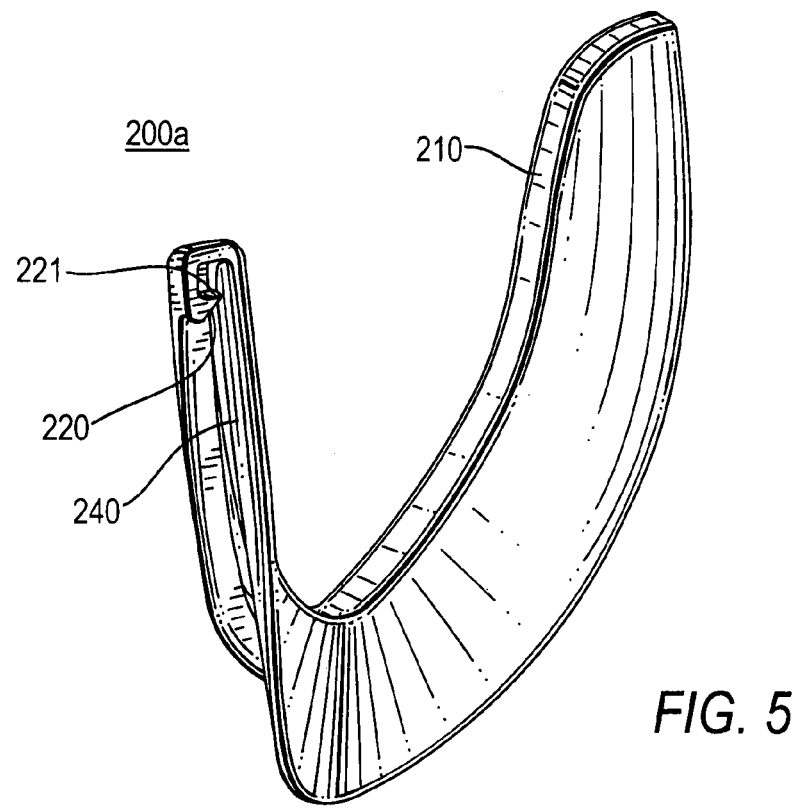
FIG. 5 is still another simplified perspective or isometric view taken generally along the line 5 in FIG. 3.

FIG. 1 shows an illustrative embodiment of the invention in a partly assembled state. FIG. 2 shows a cross section through the part of FIG. 1 that is fully assembled or complete. FIGS. 3-5 show an alternative embodiment of one component (i.e., a representative leaflet attachment fixture 200a that can be used in place of the leaflet attachment fixture 100a that is shown in FIGS. 1 and 2) in accordance with the invention. Leaflet attachment fixtures 100 (FIGS. 1 and 2) and 200 (FIGS. 3-5) are alternative to one another, although in any given valve one would tend to use a similar design for all of the leaflet attachment fixtures. Features in FIGS. 3-5 that are generally similar to features in FIGS. 1 and 2 have reference numbers (in FIGS. 3-5) that are increased by 100 from the reference numbers of the corresponding features in FIGS. 1 and 2. For example, feature 120 in FIG. 2 and feature 220 in FIGS. 3 and 5 are generally similar to one another. The various components that are shown in the FIGS. will now be described in more detail in the following paragraphs.

As shown in FIGS. 1 and 2, illustrative prosthetic heart valve 10 includes hollow, annular, stent structure 20. Stent 20 has a blood-inflow edge 22 (the lower edge as viewed in FIGS. 1 and 2). The other (upper) end of stent 20 is its blood-outflow edge 24, which is covered by leaflet material (i.e., portions 32 of leaflets 30a, 30b, and 30c). In the completed valve, leaflet material 32 is covered by fixtures 100 (only one representative fixture 100a being in place in FIG. 1). Thus the upper edge or surface 110 of fixtures 100 constitutes the actual blood-outflow edge of a finished valve 10.

The interior or lumen of stent 20 includes three flexible leaflets 30a, 30b, and 30c. Each of leaflets 30 is a sheet of flexible material. The following are some examples of flexible materials that are suitable for use as leaflets: (1) materials derived from animal or human tissue (e.g., pericardium, heart valve, venous valve, dura mater, small intestine submucosa, etc.), (2) biologically synthesized or tissue-engineered materials (e.g., collagen, fibroblast populated matrix, stem cell populated scaffold, endothelial cell seeded material, etc.), and (3) polymeric materials (e.g., silicone, polyurethane, styrene-isobutylene-styrene block copolymer, polymer-impregnated fabric mesh, etc.). Again, the above list is only illustrative and not exhaustive. The term "flexible material" as used herein includes any suitable material, such as anything from this list, functionally similar materials that have not been specifically listed, and combinations thereof.

Each leaflet 30 is shaped so that a portion 32 of the leaflet can be placed over the blood-outflow edge portion 24 of stent 20 at least substantially continuously between two annularly adjacent ones of the three commissure regions 26 of the stent. (The blood-outflow edge 24 between annularly adjacent commissure regions 26 may sometimes be referred to herein as intermediate edge portions.) A respective one of fixtures 100 can then be placed over each such leaflet portion 32 (again at least substantially continuously between two annularly adjacent ones of commissure regions 26) to hold or secure the leaflet in place to stent 20. (Edge portions 32 are sometimes referred to for convenience herein as secured edges.) Leaflets 30 are further shaped so that their edges 34 that are thus not secured to stent 20 are able to come together inside stent 20 as shown in FIG. 1 to provide a closed condition of the valve. (Edges 34 are sometimes referred to for convenience herein as free edges.) Leaflets 30 are sufficiently flexible that when (during use of the valve) blood pressure on the inflow side of the valve exceeds blood pressure on the outflow side of the valve, the free edges 34 of leaflets 30 can move apart to allow blood to pass through the valve. When blood pressure on the inflow side of the valve is no longer greater than blood pressure on the outflow side of the valve, free edges 34 come together again and prevent blood from flowing back through the valve.

Each of fixtures 100 is an elongated channel-like member (or includes a channel-like portion). The interior surface of each channel is shaped to allow an upper portion of stent 20, covered by a leaflet portion 32, to be received in the channel. In addition, the interior surface of each channel is shaped to facilitate pressing the fixture 100 onto the adjacent stent and leaflet portions, and to thereafter resist removal of the fixture from the thus-received stent and leaflet portions.

Considering first the features that facilitate pressing a fixture 100 onto stent and leaflet portions, a lower and radially outer portion 120 of the channel has an inclined, lead-in, ramp or cam shape. On the other side of the channel a lower and radially inner portion 130 of the channel has a raised bead shape. Viewed from below, surfaces 120 and 130 are initially synclinal (inclined toward one another). Accordingly, when it is desired to pass a fixture 100 down onto the stent and leaflet portions that are to be received in the channel of the fixture, surfaces 120 and 130 cam the two sides of the channel apart so that the fixture can go down over the enlarged, bead-like, upper portion 28 of stent 20. The maximum dimension D1 of stent bead 28 (in a direction that is radial of valve 10 (or transverse to the blood flow axis of the valve)) is greater than the minimum dimension D2 in that same direction between fixture channel surfaces 120 and 130. In other words, the channel entry or throat through which stent and leaflet portions 28 and 32 must pass to enter the channel is smaller or narrower (dimension D2) than the width (dimension D1) of those stent and leaflet portions. Accordingly, the sides of the fixture channel must be cammed apart by features 28 and 32 in order for fixture 100 to fit down over those leaflet and stent features. The inner surface of the channel in each fixture 100 is preferably smooth and without any sharp edges to facilitate smooth fitting of the fixture onto components 28 and 32, and also to avoid any subsequent cutting of leaflet portion 32. The outer surface of stent bead 28 is also smooth and without sharp edges for similar reasons. Fixture 100 is preferably made of a material that can elastically deform to the extent necessary for the sides of its channel to move apart as described above and to thereafter resiliently move back toward one another after the throat between surfaces 120 and 130 has passed down over leaflet and stent portions 32 and 28.

Considering first the features that facilitate pressing a fixture 100 onto stent and leaflet portions, a lower and radially outer portion 120 of the channel has an inclined, lead-in ramp or cam surface. On the other side of the channel, a lower and radially inner portion 130 of the channel has a raised bead shape. Viewed from below, surfaces 120 and 130 are initially synclinal (inclined toward one another). Accordingly, when it is desired to pass a fixture 100 down onto the stent and leaflet portions that are to be received in the channel of the fixture, surfaces 120 and 130 cam the two sides of the channel apart so that the fixture can go down over the enlarged, bead-like, upper portion 28 of stent 20. The maximum dimension or thickness D1 of stent bead 28 between its inner or luminal side and its outer or abluminal side (in a direction that is radial of valve 10 (or transverse to the blood flow axis or blood flow direction of the valve)) is greater than the minimum dimension D2 (e.g., the initial width) in that same direction between fixture channel surfaces 120 and 130. In other words, the channel entry or throat through which stent and leaflet portions 28 and 32 must pass to enter the channel has a smaller or narrower initial width (dimension D2) than the thickness (dimension D1) of those stent and leaflet portions. Accordingly, the sides of the fixture channel must be cammed apart by features 28 and 32 in order for fixture 100 to fit down over those leaflet and stent features. The inner surface of the channel in each fixture 100 is preferably smooth and without any sharp edges to facilitate smooth fitting of the fixture onto components 28 and 32, and also to avoid any subsequent cutting of leaflet portion 32. The outer surface of stent bead 28 is also smooth and without sharp edges for similar reasons. Fixture 100 is preferably made of a material that can elastically deform to the extent necessary for the sides of its channel to move apart as described above and to thereafter resiliently move back toward one another after the throat between surfaces 120 and 130 has passed down over leaflet and stent portions 32 and 28.

Considering now the features of the channel in each fixture 100 and the features of stent bead 28 that cooperate to resist removal of a fixture 100 after it has been placed on the stent, the upper or "back" side 121 of fixture feature 120 is transverse to the blood flow axis of the valve. Surface 121 faces toward a retaining surface 29a of the stent bead 28 that is also transverse, and preferably orthogonal, to the blood flow axis of the valve, as shown in FIG. 2. Accordingly, after a fixture 100 has been pressed down onto stent 20, fixture surface 121 latches under the retaining surface 29a of stent bead 28 to prevent the fixture from coming off the stent (and the leaflet portion 32 that is thus trapped between the stent and the fixture). The upper or back side of fixture bead 130 similarly cooperates with an opposite surface 29b of stent bead 28 to additionally help resist removal of a fixture 100 from stent and leaflet portions 28 and 32. In particular, surface 29b is inclined inwardly (of the valve as a whole) as one moves upwardly along that surface, which complements the inward inclination of the back side of bead 130 as one moves upwardly along that surface. Note that latching action on both the luminal and abluminal sides of stent 20 (as with inwardly projecting surfaces 120 and 130 on both sides of the entrance to the channel in fixture 100 in FIGS. 1 and 2) is optional. It may instead be sufficient to have such latching action on only one side of the stent, which is what the alternative embodiment illustrated by FIGS. 3-5 provides. Thus, in FIGS. 3-5 surface 230 is relatively smooth, and only structure 220 is provided for latching.

The "fit" or clearance between assembled elements 20 and 100 is sufficient to allow leaflet portions 32 to reside between those elements and also to apply sufficient pressure to leaflet portions 32 to hold leaflets 30 securely in place relative to elements 20 and 100. Several of the above-described structural features can assist with this securement of leaflets 30 to elements 20 and 100. These features may include (1) the relatively convoluted path that leaflet portion 32 takes in passing between elements 20 and 100, (2) constructing fixtures 100 so that the sides of their channels resiliently move back toward one another after elastically deflecting apart as each fixture is pressed on over elements 28 and 32 (such resilience applying pressure to leaflet portions 32 in the assembled valve), and (3) the latching action between complementary surfaces such as 121 and 29a (which latching action can apply additional pressure to leaflet portions 32, e.g., between the top of stent bead 24 and the extreme upper surface of the fixture channels).

Note that the use of fixtures 100 can avoid or reduce the need for sutures to hold leaflets 30 to stent 20. In the embodiment described above, three fixtures 100 are used. Each fixture 100 extends at least substantially continuously from one commissure region 26 of stent 20 to another annularly adjacent one of the commissure regions. Accordingly, each fixture 100 can do at least substantially all of the work that is required to secure a respective one of leaflets 30 to stent 20 (i.e., by covering and securing at least substantially all of the portion 32 of that leaflet to the stent). In its longitudinal direction, each fixture 100 is shaped (or includes a portion that is shaped) to follow the upper edge of stent 20 between the two commissure regions 26 between which that fixture 100 will be used (see, for example, FIGS. 3-5, which show the longitudinal shape of one representative fixture 200*a* for an alternative embodiment). Each fixture 100 or 200 may be thought of as a relatively long clip for clipping the portion 32 of an associated leaflet to the upper portion of stent 20. Fixtures 100 or 200 can apply securing force to leaflets 30 that can be widely distributed along the length of the portion 32 of each leaflet. For example, this securing force can be uniform or substantially uniform along the length of the portion 32 of each leaflet. This is in contrast to suture attachment, which tends to concentrate securement force at the spaced locations where the suture material passes through the leaflet material. Fixtures 100 or 200 can also avoid perforation of leaflets 30 for purposes of the final (long-term) securement of the leaflets to stent 20. The amount and distribution of leaflet securement force is a function of manufacture (preferably automated or at least largely automated) of components like 20 and 100 or 200, and not of operator skill or proficiency as in the case of leaflet securement by suturing. Accordingly, more uniform and repeatable results can be achieved.

Note that each fixture 100 or 200 is curved along its length to follow the arc of stent 20 about the axis of blood flow through the valve, and also to follow the down-and-up curvature of the outflow edge 24 of stent 20 between a pair of annularly adjacent commissure regions 26. This last-mentioned curvature is due to the fact that stent 20 is "high" at each commissure region 26, but that its outflow edge 24 dips down between each such pair of annularly adjacent commissure regions.

If desired, multiple fixtures 100 or 200 may be combined into one fixture structure, which may be annular or substantially annular.

Another advantageous feature of the invention is that the lower and radially inner surfaces of fixtures like 100 can be shaped to influence leaflet operation and/or performance in various ways. The relevant portion of a fixture surface is indicated generally by the reference number 140 in FIG. 2. (Surface 240 in FIGS. 3-5 is different than surface 140 in the respects being discussed here. Accordingly, FIGS. 3-5 illustrate the point that what is being discussed here is optional and does not need to be included if not desired.)

As an example of how a surface 140 can be shaped and/or positioned to affect leaflet operation, that surface can be rounded or otherwise shaped to distribute flexure of the adjacent portion of the associated leaflet 30 over a larger area than might otherwise be the case as the leaflet flexes to open and close the valve. Considering first the geometry when the valve is closed, the radius of curvature of surface 140 (in a plane that is a transverse cross section of fixture 100 (e.g., as indicated by the cross-hatching in FIG. 2)) may be somewhat smaller than the radius of curvature of the adjacent portion of representative leaflet 30*a*. These curves of surface 140 and leaflet 30*a* converge toward one another in the direction toward stent 20, but they gradually diverge from one another as one moves inwardly from the stent. As leaflet 30*a* begins to open, more of the leaflet begins to contact more of surface 140 (in the direction inwardly from stent 20). In other words, more and more of leaflet 30*a* rolls up against surface 140. By giving surface 140 a radius of curvature that is less than the radius of curvature of the adjacent portion of closed leaflet 30*a* but more than what would (in the absence of surface 140) be the radius of curvature of that portion of open leaflet 30*a*, one can use surface 140 to distribute flexure of this portion of the leaflet over a larger such portion of the leaflet. This helps to convert flexure of leaflet 30*a* from something that can be like folding or creasing, and instead makes that flexure more widely distributed and therefore less locally severe. This can extend the service life of the leaflets. The lower and radially inner surface(s) of fixtures 100 can be shaped in any desired way to beneficially affect leaflet motion and/or operation in any desired way.

Recapitulating at least some of the above, a leaflet attachment fixture 100 or 200 conformed to the outflow rim 24 of the stent 20 can be used to attach flexible leaflets 30 to the stent without perforating the leaflets. The fixture 100 or 200 simplifies the manufacturing process and provides consistent and reliable attachment. Using the fixture 100 or 200 eliminates stress concentration points and can also shape the local geometry of the leaflet 30 at the attachment site to further facilitate a preferred leaflet configuration for load distribution, contact control, or other types of leaflet function.

FIG. 1 shows an example of one type of attachment fixture 100*a* assembled with a leaflet 30*a* and a stent 20. In this particular assembly, the leaflet 30*a* is first placed against the outer surface of the stent 20. The attachment fixture 100 is snapped in place along the outflow rim 24, clamping the leaflet onto the stent (see also FIG. 2). The attachment fixture 100 can have features (e.g., 121, etc.) for engaging to the stent, as well as "end-effector(s)" (e.g., 140) to facilitate leaflet configuration along the attachment edge. The fixture 100 could also be further secured to the stent 20 using sutures or other attachment means. The configuration of the engagement feature (e.g., 121/29*a*) and the end effector (e.g., 140) can vary along the length of the fixture 100. The fixture can be a single continuous piece or multiple pieces placed along the outflow rim 24 of the stent 20. The fixture 100 can also have cut-outs strategically located for structural, attachment, or other purposes. Fixture 200 is another example of a fixture that can have features similar to at least some of those described above for fixture 100.

The fixture 100 or 200 can be made of any suitable materials, such as metal, polymer, or a composite that possesses the desired physical and chemical properties. The surface of the fixture 100 or 200 can be treated with various methods to enhance blood compatibility, cell attachment, and/or tissue covering.

Figure 6:
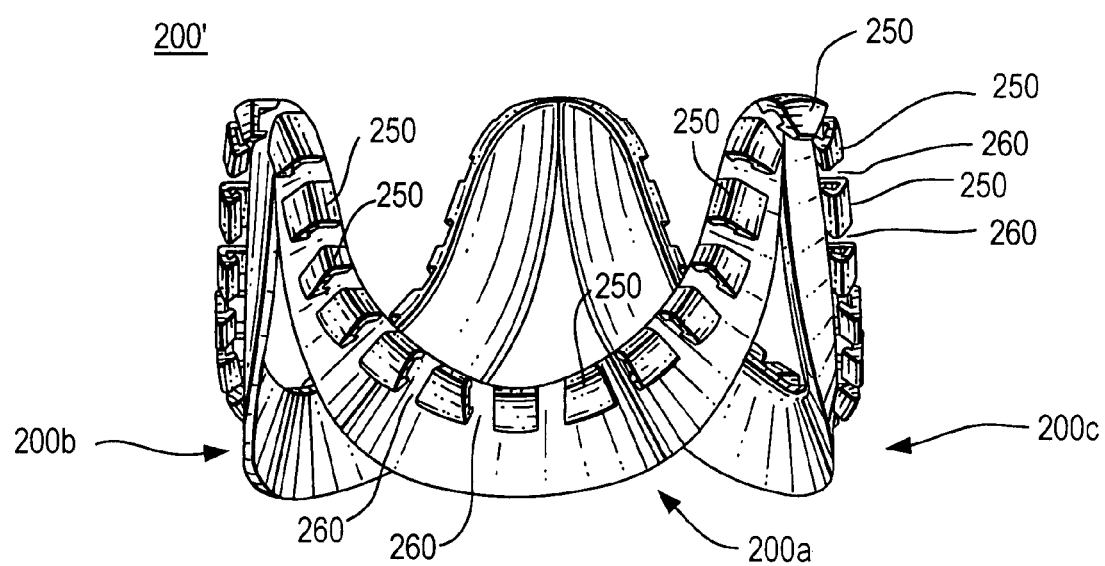
FIG. 6 is a simplified elevational view showing a portion of another illustrative embodiment in accordance with the invention.

FIG. 6 illustrates some possibilities for modification of the fixture structure in accordance with the invention. Reference numbers in the 200 series are used again in FIG. 6 to avoid undue proliferation of different reference numbers. In FIG. 6 fixture 200' is one annular structure that extends all the way around an assembled valve. This annular structure has three portions 200*a*, 200*b*, and 200*c*, each of which can be somewhat like fixture 200*a* in FIGS. 3-5. A difference from what is shown in FIGS. 3-5, however, is that the channel portion of fixture structure 200' is interrupted rather than continuous as in the earlier FIGS. Thus the channel structure of fixture 200' includes many segments 250 that are spaced from one another along the outflow edge portion 210 of the fixture. Annularly adjacent ones of channel segments 250 are spaced from one another by gaps 260 where the channel is interrupted or omitted. Each of channel segments 250 has a cross-sectional shape like that described earlier for the continuous channel embodiments. Each channel segment 250 therefore operates like a clip to hold the adjacent portion of a valve leaflet to the adjacent portion of the valve stent. Channel segments 250 are provided in sufficient numbers and with sufficient annular extent and annular distribution that they provide good securement for the leaflets all the way around the valve, even though the leaflet-securing channel structure is not as continuous as it is in the earlier-described embodiments. For example, channel segments 250 are, at least on average, preferably larger in annular extent than the average annular extent of the gaps 260 between the channel segments. Thus channel segments 250 collectively preferably cover more than half of the annulus of leaflet material adjacent the outflow edge of an assembled valve. A fixture or clip structure 100, 200, or 200' with a channel structure that is either substantially continuous or that has segments having characteristics like those described in connection with FIG. 6 may be said to substantially cover the portion of a leaflet that is placed over the blood-outflow edge of the valve stent. Such a fixture or clip structure 100, 200, or 200' may also be said to secure a leaflet to the valve stent at least substantially continuously between the commissure regions between which that leaflet is disposed.

It will be understood that the foregoing is only illustrative of the principles of the invention, and that various modifications can be made by those skilled in the art without departing from the scope and spirit of the invention. For example, although the invention is illustrated in the context of a three-leaflet valve having three commissure regions 26 and a blood-outflow edge 24/110 that is scalloped or undulating in a particular way in the annular direction, a valve in accordance with the invention could alternatively have a different number of leaflets, a different number of commissures, and/or a different outflow edge configuration.

What is claimed is:

1. A prosthetic heart valve, comprising:
   a hollow, annular, stent structure having a blood-inflow edge and a blood-outflow edge, the blood-outflow edge defining portion that includes a plurality of commissure regions spaced from one another a plurality of intermediate edge portions interposed between the commissure regions, each intermediate edge portion having a midpoint between adjacent commissure regions, the blood-outflow edge having a luminal side and an abluminal side, the blood-outflow edge in the commissure regions being spaced from the blood-inflow edge by first distances, and the blood-outflow edge in the intermediate edge portions being spaced from the blood-inflow edge by a second distance less than the first distances;
   a plurality of leaflets, each leaflet having a portion positioned over the intermediate edge portion between respective pairs of annularly adjacent ones of the commissure regions, the portion of at least one of the leaflets and the intermediate edge portion between at least one of the respective pairs of commissure regions collectively defining a receiving structure; and
   a clip structure having first and second legs spaced apart so as to define a channel therebetween, the clip structure being connected to the receiving structure in an assembled position with the first leg on the luminal side of the blood-outflow edge and the second leg on the abluminal side of the blood-outflow edge, wherein the clip structure in the assembled position extends along and beyond the midpoint of the intermediate edge portion extending between the at least one of the respective pairs of commissure regions.

2. The prosthetic heart valve defined in claim 1, wherein the stent structure and the clip structure include interengaging shapes for securing the clip structure to the receiving structure in the assembled position.

3. The prosthetic heart valve defined in claim 2, wherein material of the at least one leaflet is interposed between the interengaging shapes in the assembled position.

4. The prosthetic heart valve defined in claim 2, wherein the interengaging shapes are shaped to facilitate placement of the clip structure on the receiving structure but to thereafter resist removal of the clip structure from the receiving structure.

5. The prosthetic heart valve defined in claim 4, wherein the clip structure is configured to elastically deform during placement of the clip structure on the receiving structure and to thereafter resiliently apply clamping pressure to the at least one leaflet against the stent structure.

6. The prosthetic heart valve defined in claim 1, wherein the clip structure includes a clip surface that can be contacted by a portion of the at least one leaflet that moves during use of the prosthetic heart valve.

7. The prosthetic heart valve defined in claim 6, wherein the clip surface is shaped to increase the radius of curvature of flexure of the portion of the at least one leaflet that contacts the clip surface during use of the prosthetic heart valve.

8. The prosthetic heart valve defined in claim 1, wherein the stent structure has a lumen extending in a blood flow direction and the receiving structure has a thickness in directions radial to the blood flow direction, and
   the channel in the clip structure has an open end opposite a closed end, the open end having an initial width between the first and second legs when the clip structure is apart from the receiving structure, the initial width being less than the thickness of the receiving structure.

9. The prosthetic heart valve defined in claim 8, wherein the first and second legs of the clip structure are biased toward the initial width, and are movable away from one another to a dimension greater than the initial width for connection of the clip structure in the assembled position to the receiving structure.

10. The prosthetic heart valve defined in claim 9, wherein one of the first and second legs of the clip structure includes a cam surface for engaging the receiving structure and moving the one of the first and second legs away from the other of the first and second legs during connection of the clip structure in the assembled position to the receiving structure.

11. The prosthetic heart valve defined in claim 8, wherein the stent structure has a retaining surface on at least one of the luminal side or the abluminal side, the retaining surface extending in a direction orthogonal to the blood flow direction, and
   the clip structure has an engagement surface on at least one of the first and second legs, the engagement surface extending in the direction orthogonal to the blood flow direction in the assembled position, the engagement surface of the clip structure engaging the retaining surface of the stent structure in the assembled position to resist removal of the clip structure from the receiving structure.

12. The prosthetic heart valve defined in claim 1, wherein the portion of the at least one leaflet is positioned over the intermediate edge portion substantially continuously between the at least one of the respective pairs of commissure regions.

13. The prosthetic heart valve defined in claim 1, wherein the clip structure in the assembled position extends substantially continuously between at least one of the respective pairs of commissure regions.

* * * * *

UNITED STATES PATENT AND TRADEMARK OFFICE
CERTIFICATE OF CORRECTION

PATENT NO.         : 8,092,523 B2                                    Page 1 of 1
APPLICATION NO.    : 11/717305
DATED              : January 10, 2012
INVENTOR(S)        : XueMei Li et al.

It is certified that error appears in the above-identified patent and that said Letters Patent is hereby corrected as shown below:

Column 3, line 19, delete "," after "lead-in".
Column 3, line 20, delete "shape" and insert therefor --surface--.
Column 3, line 20, after "channel" insert --,--.
Column 3, line 28, after "dimension" insert --or thickness--.
Column 3, line 29, after "28" insert --between its inner or luminal side and its outer or abluminal side--.
Column 3, line 30, after "axis" insert --or blood flow direction--.
Column 3, line 31, after "D2" insert --(e.g., the initial width)--.
Column 3, line 34, delete "is" and insert --has a--.
Column 3, line 35, after "narrower" insert --initial width-- and delete "width" and insert --thickness--.
Column 7, line 38, after "defining" insert --a--.
Column 7, line 39, after "another" insert --and--.

Signed and Sealed this
Ninth Day of April, 2013

Teresa Stanek Rea
*Acting Director of the United States Patent and Trademark Office*